United States Patent [19]

Clerici et al.

[11] Patent Number: 5,126,491
[45] Date of Patent: Jun. 30, 1992

[54] PROCESS FOR OXIDATING PARAFFINIC COMPOUNDS

[75] Inventors: Mario G. Clerici, San Donato Milanese; Bartolomeo Anfossi, Milan; Giuseppe Bellussi, Piacenza, all of Italy

[73] Assignee: Eniricerche S.p.A., Milan, Italy

[21] Appl. No.: 562,129

[22] Filed: Aug. 3, 1990

[30] Foreign Application Priority Data

Aug. 9, 1989 [IT] Italy ................... 21492 A/89

[51] Int. Cl.$^5$ ............................................. C07C 45/28
[52] U.S. Cl. .................................. 568/342; 568/385; 568/910; 568/910.5; 558/440; 558/451
[58] Field of Search ............... 568/342, 385, 910.5, 568/910; 558/440, 451

[56] References Cited

U.S. PATENT DOCUMENTS

| | | | |
|---|---|---|---|
| 3,879,467 | 4/1975 | Zajacek et al. | 568/910 |
| 4,310,704 | 1/1982 | Mimoun et al. | 568/342 |
| 4,480,135 | 10/1984 | Esposito et al. | 568/385 |
| 4,918,238 | 4/1990 | Costantini et al. | 568/385 |
| 4,978,800 | 12/1990 | Sanderson et al. | 568/385 |
| 5,021,607 | 6/1991 | Huybrechts | 568/385 |

FOREIGN PATENT DOCUMENTS 1147707  3/1985  U.S.S.R. ................... 568/385

*Primary Examiner*—James H. Reamer
*Attorney, Agent, or Firm*—Shea & Gould

[57] ABSTRACT

Process for oxidating paraffinic compounds in order to yield the corresponding alcoholic and/or ketonic compounds, which process consists of reacting said paraffins with an aqueous solution of hydrogen peroxide, possibly dissolved in a solvent, by operating at a temperature comprised within the range of from 0° C. to 100° C., in the presence of a titanium-silicalite of formula $$pHMO_2 \cdot qTiO_2 \cdot SiO_2$$

wherein
M is a metal selected from among aluminum, gallium and iron,
p is comprised within the range of from 0 to 0.05 and
q is comprised within the range of from 0.0001 to 0.04, and the $H^+$ of $HMO_2$ can be least partially replaceable or replaced by cations.

9 Claims, No Drawings

PROCESS FOR OXIDATING PARAFFINIC COMPOUNDS

The present invention relates to a process for oxidating paraffinic compounds in order to yield the corresponding alcoholic and/or ketonic compounds, using $H_2O_2$ and, as the catalyst, a titanium-silicalite of formula $$pHMO_2 \cdot qTiO_2 \cdot SiO_2$$

wherein

M is a metal selected from among aluminum, gallium and iron, p is comprised within the range of from to 0.05, including O, and q is comprised within the range of from 0.0001 to 0.05. and the $H^+$ of $HMO_2$ can be partially replaceable or replaced by cations.

It is known that paraffins are poorly reactive compounds and in order to functionalize them high temperatures or considerably strong reactants such as, e.g., ozone, trifluoroperacetic acid, chromic acid, permanganate are necessary. Of course, so severe conditions result in unsatisfactory selectivity values: the oxidation of, e.g., straight paraffins, with oxygen requires temperatures close to 150° C. and leads to the formation of a complex mixture of products containing, among others, acids, ketones, alcohols and peroxides, some derivating from the fragmentation of the paraffinic compound (N. M. Emanuel, E. T. Denisov, Z. K. Maizus, "Liquid-Phase Oxidation of Hydrocarbons", Plenum Press, New York, 1967).

The oxidation of paraffinic compounds by means of hydrogen peroxide or of peroxy compounds in general is reported as well. It is carried out in the presence of metal complexes as catalysts. However, rather low yields are generally obtained, as referred to the peroxy reactant, owing to parallel reactions of decomposition to oxygen (J. T. Groves, G. A. McClusky, J.A.C.S. page 859, 1976; J. B. Vincent et al., J.A.C.S. page 6898, 1988; R. H. Fish et al., J.C.S. Chem. Commun. page 1504, 1988).

As the catalyst for the oxidation of paraffins with hydrogen peroxide generated in situ, also a zeolite of 5A type was used in the past, on which metal palladium and iron ion were deposited (N. Herron et al., J.A.C.S. page 2837, 1987). In this case too, the reaction yields are poor.

The present Applicant has surprisingly found now that paraffinic compounds can be oxidated in order to yield the corresponding alcoholic and/or ketonic derivatives by means of hydrogen peroxide and operating at low temperatures, with high values of conversion and selectivity being achieved, as referred to both said reactants.

The object of the instant invention is hence a process for oxidating, in order to yield the corresponding alcoholic and/or ketonic compounds, with hydrogen peroxide, by using a titianium-silicalite as the catalyst, paraffinic compounds of general formula:

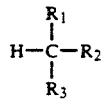

wherein $R_1$ and $R_2$ are selected from among: linear alkyl of from 1 to 20 carbon atoms, branched or cyclic alkyl of from 3 to 20 carbon atoms; or $R_1$ and $R_2$ together with each other can constitute a divalent radical which, by being closed on the carbon atom they are linked to, generates a ring structure.

$R_1$ and $R_2$ can be either equal to, or different from, each other and can also contain such functional groups as: chlorine, bromine, iodine, fluorine, nitro group, alkoxy, amino group, carbonyl group, carboxy group, carboxy ester group, nitrile group and amide.

$R_3$ has the same meaning as of $R_1$ and $R_2$, or is hydrogen.

The titanium-silicalites used as the catalysts in the process according to the present invention are disclosed in Italian patents Nos. 1,207,519; 1,207,520; in U.S. Pat. Nos. 4,666,692; 4,410,501; 4,701,428 and in Italian patent No. 1,213,363 and 1,213,504, and are represented by the following general formula, expressed as the molar ratios of oxides (in its calcined, anhydrous form):

$$pHMO_2 \cdot qTiO_2 \cdot SiO_2$$

wherein p is comprised within the range of from 0 to 0.05, with 0 being included among the possible values, and q is comprised within the range of from 0.0001 to 0.05, and is preferably is comprised within the range of from 0.01 to 0.025.

The use of such catalysts in the process of hydroxylation of aromatic hydrocarbons (Italian patent No. 1,150,699) and of epoxidation of olefinic compounds (Italian patent No. 1,152,299), both carried out in the presence of hydrogen peroxide, was already described in the past.

Some specific examples of paraffinic compounds which can be oxidated by means of the method according to the present invention, are: propane, n-butane, isobutane, n-pentane, n-hexane, cyclohexane, chlorohexane, methyl heptanoate, amylonitrile, dodecane.

The reaction products obtained by means of the process according to the present invention are oxygen-containing compounds, deriving from the oxidation of substantially one single carbon atom of the paraffinic compound used as the starting compound. Therefore, monoalcohols or ketones or mixtures thereof are obtained —depending on the paraffinic compound used as the starting compound and of the reaction conditions—with a very good selectivity.

The process according to the present invention is carried out in practice by reacting the two reactants, i.e., the paraffin and hydrogen peroxide, in the presence of titanium-silicalite, at a temperature comprised within the range of from 0° C. to 100° C., possibly in an autoclave, according to the nature of the paraffin and of the solvent.

The reaction takes place within a rather short time, and the reaction time is generally comprised within the range of from a few minutes to some hours, still depending on the other reaction parameters and of the nature of the paraffinic compound. Reaction times comprised within the range of from 10 minutes to 4 hours can be advantageously used.

The reaction can be carried out in a solventless system or in the presence of an inert solvent, either under the autogenous system pressure, or under room pressure, either batchwise or continuously, with the reaction products being separated from the effluent and any unconverted reactants being recycled to the reaction.

Suitable solvents for this process can be methanol, tert.-butyl alcohol, acetonitrile, acetone, water or mixtures thereof. In some cases, the product(s) from the oxidation reaction can be advantageously used as the solvent.

The operating temperature is preferably comprised within the range of from 25° C. to 70° C.

Hydrogen peroxide in used in aqueous solution at a concentration comprised within the range of from 1 to 70% by weight/volume, and the molar ratio of the paraffin to hydrogen peroxide is selected within the range of from 0.5 to 100, and preferably of from 1 to 10.

The following examples are supplied for the purpose of merely illustrating the invention, and in no way shall they be construed as being limitative of the same invention.

Examples from 1 to 3 describe the preparation of the catalysts useful in the process according to the present invention.

Examples from 4 to 9 and from 13 to 17 illustrate the process according to the present invention, carried out by using the catalysts described in Examples from 1 to 3.

Examples from 10 to 12 are reported for comparative purposes, and do not fall within the purview of the present invention.

EXAMPLE 1

A TS-1 titanium-silicalite is prepared according to as indicated in U.S. Pat. No. 4,410,501.

A solution obtained by dissolving 230 g of tetraethyl titanate in 4,160 g of tetraethyl silicate is added with vigorous stirring to 7,250 g of a solution at 14% of tetrapropylammonium hydroxide. The resulting mixture is kept with strong stirring until a single-phase, clear solution is obtained. Said solution is then diluted with 8,165 g of demineralized water.

The so obtained solution is charged to an autoclave and is kept heated 4 hours at 170° C. under its autogenous pressure.

The reaction product is discharged from the autoclave, is centrifuged and the centrifugation cake is washed twice by being re-dispersed and centrifuged again. The centrifugation cake is calcined in air for 5 hours at 550° C., and at the end it, at the I.R. and R.X. analyses, shows to be a titanium-silicalite (TS-1), whose composition, in its calcined and anhydrous form, is the following:

0.023 $TiO_2$; $SiO_2$.

EXAMPLE 2

497 g of $TiOCl_2$ is dissolved in 26,350 g of an aqueous solution of tetrapropylammonium hydroxide (TPA/OH—) at 14% by weight, and 14,538 g of colloidal silica at 30% is added with vigorous stirring to said solution. The resulting mixture is heated to 60° C. and is kept stirred at that temperature for about 2 hours; then 29,680 g of demineralized water is added and the resulting mixture is stirred for one further hour, still at 60° C.

The clear solution, having the following molar composition:

5 TPA—OH; $TiO_2$; 20 $SiO_2$; 800 $H_2O$ is charged to an autoclave equipped with stirring means, is heated to 170° C. and is kept stirred at this temperature for a three-hours time.

The so obtained suspension, of milky appearance, containing in suspension zeolite microcrystals, is centrifuged and the centrifugation cake is washed by being redispersed in water; the zeolite product is then totally recovered by means of a following centrifugation (3,500 g of titanium-silicalite).

In the mean time, 1,346 g of tetraethyl silicate is added with vigorous stirring to 1,437 g of solution at 12% by weight of tetrapropylammonium hydroxide and the resulting mixture is heated 1 hour at 60° C. Then 5,890 g of demineralized water is added and the mixture is kept stirred for a further hour. A clear solution is so obtained, in which the previously prepared titanium-silicalite is carefully dispersed.

The resulting suspension of milky appearance is fed to a spray-dryer (a NIRO ATOMIZER disk drier; temperature of entering air 300° C.; temperature of leaving air 120° C.; chamber diameter 1.5 m), with compact microspheres being obtained, which have an average diameter close to 20 μm.

The atomized product is charged to a muffle under an $N_2$ atmosphere and is heated up to 550° C. After a 2-hours stay at that temperature under an $N_2$ atmosphere, said atmosphere is gradually turned from $N_2$ into air, and the product is allowed to rest for a further 2 hours at 550° C. in air. The so obtained catalyst has the following chemical composition, as mol ratio:

1 $TiO_2$; 43 $SiO_2$.

EXAMPLE 3

27 g of aluminum isopropylate is dissolved in 5400 g of solution at 18.7% by weight of tetrapropylammonium hydroxide. In a separate vessel, 230 g of tetraethyl orthotitanate is dissolved in 4160 g of tetraethyl silicate and this solution is added with stirring to the preceding one.

The resulting reaction mixture is heated up to 50°-60° C., and is kept at this temperature, still with stirring, until a single-phase solution is obtained; 10,000 cc of water is then added.

The so obtained solution is charged to an autoclave and is heated, under its autogenous pressure, up to 170° C., then is kept 4 hours at this temperature.

The product is discharged from the autoclave, is centrifuged and the centrifugation cake is washed twice by re-dispersion and centrifugation. A portion of the washed centrifugation cake is calcined 5 hours in air at the temperature of 550° C., and at the end it is shown to be a zeolite having, in its anhydrous form, the following composition:

0.0081 $Al_2O_3$; 0.0250 $TiO_2$; $SiO_2$.

EXAMPLES 4-9

2.5 ml of distilled n-hexane and about 1.5 ml of $H_2O_2$ at 33% by w/v are dissolved in 25 ml of solvent. The exact titre of hydrogen peroxide is determined by iodometric titration.

Then 0.5 g of catalyst is added to the solution maintained at the controlled temperature of 55° C., and the resulting reaction mixture kept strongly stirred.

At regular time intervals, small aliquots of suspension are drawn in order to determine the concentration of hydrogen peroxide and the reaction products. The amounts of these latter are determined by gas-phase chromatography, by means of the method of the internal standard (2.3 m long glass column, packed with LAC 728 at 20% on Chromosorb, T=100° C.).

The nature of the products is confirmed by mass-spectrometry.

The results are reported in Table 1.

The autoclave is placed in a temperature-controlled bath at 55° C., with strong stirring, and the inner autoclave pressure is adjusted at 3 atm with isobutane.

120 minutes later, the reaction is quenched, the excess of isobutane is vented and the concentration of $H_2O_2$ is determined. The concentration of tert.-butyl alcohol is determined by gas-chromatography (1.8 m long column, packed with Poropack, T=120° C.) and the product is confirmed by mass-spectrometry.

TABLE 1

| Example | Catalyst prepared as in: | Solvent | $H_2O_2$ (M/l) | Time (min) | Conversion of $H_2O_2$ (%) | 2-Hexanol (M/l) | 2-Hexanone (M/l) | 3-Hexanol (M/l) | 3-Hexanone (M/l) |
|---|---|---|---|---|---|---|---|---|---|
| 4 | Ex. 1 | Tert.-butanol | 0.498 | 90 | 90 | 0.0203 | 0.131 | 0.0717 | 0.0280 |
| 5 | Ex. 1 | Methanol | 0.507 | 140 | 94 | 0.0470 | 0.147 | 0.0683 | 0.0224 |
| 6 | Ex. 1 | Acetonitrile | 0.512 | 165 | 65 | 0.0279 | 0.0207 | 0.0734 | 0.0455 |
| 7 | Ex. 3 | Methanol | 0.560 | 210 | 92 | 0.0483 | 0.142 | 0.0652 | 0.0186 |
| 8 | Ex. 2 | Tert.-butanol | 0.502 | 90 | 88 | 0.0201 | 0.132 | 0.0706 | 0.0273 |
| 9 | Ex. 1 | Methanol | 0.855* | 135X | 85 | 0.0430 | 0.205 | 0.0880 | 0.0260 |

*2.5 cc of $H_2O_2$ were used

EXAMPLES 10-12

Zeolite H-ZSM5 was prepared according to Example 1 of U.S. Pat. No. 3,702,886.

Boralite was obtained according to Example 4 of Italian patent No. 1,166,822.

The catalyst constituted by a dispersion of $TiO_2$ on amorphous silica was obtained according to Example 1 of U.S. Pat. No. 3,923,843.

The so obtained compounds are used according to the modalities as already disclosed in Examples 4-9.

The results are reported in Table 2.

$H_2O_2$ conversion=50%, tert.-butyl alcohol 2.10 mmol.

EXAMPLE 15

5 cc of cyclohexane and 1.5 cc of $H_2O_2$ are dissolved in 25 cc of tert.-butyl alcohol.

The exact titre of hydrogen peroxide results to be 0.510M.

0.51 g of the catalyst prepared in Example 1 is added with stirring to 30 cc of this solution, kept at the temperature of 74° C. After 120 minutes the conversion of

TABLE 2

| Example | Catalyst | Solvent | $H_2O_2$ (M/l) | Time (min) | Conversion of $H_2O_2$ (%) | 2-Hexanol (M/l) | 2-Hexanone (M/l) | 3-Hexanol (M/l) | 3-Hexanone (M/l) |
|---|---|---|---|---|---|---|---|---|---|
| 10 | H-ZSM5 | Methanol | 0.545 | 270 | 25 | — | — | — | — |
| 11 | Boralite | Methanol | 0.547 | 250 | — | — | — | — | — |
| 12 | $TiO_2$—$SiO_2$ | $H_2O$* | | 50X | 60 | — | — | — | — |

*T = 65° C., 3 ml of $H_2O_2$ at 33% by weight/volume

EXAMPLE 13

4 ml of n-hexane is added to a suspension of 0.5 g of catalyst prepared as disclosed in Example 1, in 25 ml of aqueous $H_2O_2$ at the concentration of 0.585M, maintained at the controlled temperature of 56° C. and kept stirred by means of a magnetic stirrer.

The titre of hydrogen peroxide is checked at regular time intervals, and after 120 minutes the reaction is discontinued. The liquid phase is homogenized by means of the addition of tert.-butyl alcohol and methanol, and the reaction products are then determined analogously to the preceding Exampes.

The reaction products are contituted by 0.055 mmol of 2-hexanol, 2.02 mmol of 2-hexanone, 0.328 mmol of 3-hexanol, 1.34 mmol of 3-hexanone.

EXAMPLE 14

20 cc of a 0.605M solution of hydrogen peroxide in methanol (obtained by mixing 25 cc od methanol and about 1.6 cc of $H_2O_2$ at 32% by weight/volume) is charged to a glass autoclave together with 0.4 g of catalyst prepared as described in Example 1.

$H_2O_2$ results to be of 49%.

The reaction products are identified and quantified by gas-chromatography and mass spectrometry (2.3 m long glass column, packed with LAC 728 at 20% on Chromosorb, T =120° C.).

Cyclohexanol 0.58 mmol; cyclohexanone 0.92 mmol.

EXAMPLE 16

1.5 cc of n-decane, 1.5 cc of $H_2O_2$ at 33% by weight/volume and 25 cc of methanol (titre of $H_2O_2$=0.552M) are heated to 61° C., and are kept at this temperature. 0.5 g of titanium silicalite (Example 1) is added with strong stirring; 105 minutes later a further 2 ml of n-decane is added.

After 165 minutes, the conversion of $H_2O_2$ is of 93%. The reaction products are identified and quantified by GLC and mass spectrometry.

2-decanol (0.656 mmol); 3-decanol and 4-decanol (1.10 mmol); 2-decanone (1.73 mmol); 3-decanone and 4-decanone (1.41 mmol).

EXAMPLE 17

2.5 cc of 1-chlorohexane and 1.5 cc of $H_2O_2$ at 33% by weight/volume (titre of $H_2O_2$=0.557 mol/liter) are reacted in the same way as of Example 5. After 4 hours, residual hydrogen peroxide is 3%. The reaction products are identified by GLC and mass spectrometry (LAC column, T=160° C.).

1-chloro-5-hexanol (0.36 mmol); 1-chloro-4-hexanol (0.93 mmol); 1-chloro-5-hexanone (0.10 mmol); 1-chloro-4-hexanone (2.10 mmol).

We claim:

1. Process for producing paraffinic compound derived alcoholic and/or ketonic derivatives, comprising oxidating a single carbon atom of paraffinic compounds selected from the group consisting of propane, butane, isobutane, n-pentane, n-hexane, cyclohexane, chloroexane, methyl heptanoate, amylonitrile, n-decane and dodecane with hydrogen peroxide in the presence of a titanium-silicalite having the following general formula $$pHMO_2 \cdot qTiO_2 \cdot SiO_2$$

wherein

M is a metal selected from among aluminum, gallium and iron, p is comprised within the range of from greater than 0 to 0.05, and q is comprised within the range of from 0.0001 to 0.05, and is preferably comprised within the range of from 0.01 to 0.025.

2. Process according to claim from 1 to 3, characterized in that the oxidation of the paraffinic compound leads to the production of monoalcohols and/or ketones, or of mixtures thereof.

3. Process according to claims from 1 to 4, characterized in that the oxidation is carried out at temperatures comprised within the range of from 0° C. to 100° C.

4. Process according to claim 3, characterized in that the oxidation is carried out at temperatures comprised within the range of from 25° C. to 70° C.

5. Process according to claims from 1 to 6, characterized in that the oxidation is carried out in the presence of a solvent selected from among methanol, tert.-butyl alcohol, acetonitrile, acetone, water or mixtures thereof.

6. Process according to claim 5, characterized in that the product from the oxidation reaction is used as the solvent.

7. Process according to claims from 1 to 8, characterized in that the oxidation is carried out under pressure.

8. Process according to claims from 1 to 9, characterized in that hydrogen peroxide is used, which is at a concentration comprised within the range of from 1 to 70% by weight/volume.

9. Process according to claims from 1 to 10, characterized in that the molar ratio of the paraffinic compound to hydrogen peroxide is selected within the range of from 0.5 to 100, and preferably of from 1 to 10.

* * * * *